United States Patent [19]

Ober

[11] Patent Number: 4,669,477

[45] Date of Patent: Jun. 2, 1987

[54] APPARATUS AND METHOD FOR PREVENTING BRUXISM

[75] Inventor: Stephen H. Ober, Salt Lake City, Utah

[73] Assignee: Empi, Inc., Fridley, Minn.

[21] Appl. No.: 735,592

[22] Filed: May 20, 1985

[51] Int. Cl.[4] .............................................. A61N 1/36
[52] U.S. Cl. .................................... 128/421; 128/777; 128/782
[58] Field of Search ............... 128/732, 774, 777, 782, 128/787, 905, 422, 423 R, 1 R, 421

[56] References Cited

U.S. PATENT DOCUMENTS

| | | | |
|---|---|---|---|
| 3,628,538 | 12/1971 | Vincent et al. | 128/422 |
| 3,797,500 | 3/1974 | Porter | 128/422 |
| 4,220,142 | 9/1980 | Rosen et al. | 128/1 R |
| 4,408,609 | 10/1983 | Axelgaard | 128/421 |

Primary Examiner—William E. Kamm
Attorney, Agent, or Firm—Kinney & Lange

[57] ABSTRACT

Apparatus for producing an electrical stimulation signal adapted to be applied to a patient's jaw muscle, thereby causing the jaw to open and preventing bruxism. The apparatus includes electrodes positioned to sense an electromyographic (EMG) signal indicative of jaw muscle activity and jaw clenching. A control circuit produces a control signal when the EMG signal exceeds a threshold value indicative of a predetermined level of jaw muscle activity. Stimulator means produce the stimulation signal in the form of a pulse train when triggered by the control signal. The threshold value and intensity of the stimulation signal are adjustable.

28 Claims, 3 Drawing Figures 4,669,477

APPARATUS AND METHOD FOR PREVENTING BRUXISM

BACKGROUND OF THE INVENTION

1. Field of the Invention

The present invention relates to electrical neuromuscular stimulators. In particular, the present invention is a stimulator for preventing bruxism.

2. Description of the Prior Art

Bruxism, the grinding or clenching of teeth during sleep, is a leading cause of temporal mandibular joint dysfunction and abnormal wearing of molar teeth. This affliction is believed to be caused by two phenomena. The first is maloclusion, the faulty closure of teeth. The second is psychological stress. As a learned behavior and an outlet from psychological stress, bruxism is exceedingly difficult to treat because it occurs during sleep when conscious activity and volitional control are non-existant.

A common method of treating bruxism involves placing a splint between dental surfaces during sleep. While a device of this type will alleviate some of the effects of bruxism, it is of no help in preventing the underlying problem. The same can be said for many of the devices disclosed in the patent literature. The Samelson U.S. Pat. Nos. 4,169,473, and 4,304,227 disclose a device for treatment of snoring and bruxism. The device is molded for cooperation with the upper and lower dental surfaces and eliminates nocturnal tooth grinding when positioned within the mouth of the user.

The Benjamin U.S. Pat. No. 4,114,612 is a device for relieving muscular tension of the head-neck region of a user. Symptoms of head and neck tension are said to include the grinding of teeth during sleep. The Rosen et al U.S. Pat. No. 4,220,142 is a behavior-shaping device for eliminating nocturnal sounds, such as snoring. An alarm is activated to wake the user when a predetermined level of sound is sensed. It is said that the device can be used to treat bruxism.

It is evident that there is continuing need for bruxism prevention and treatment apparatus. Apparatus which inhibit bruxism by breaking it as a learned behavior pattern, rather than merely alleviating its effects, would be especially desirable. This apparatus should operate without disturbing the user's sleep. It must also be effective and convenient to use.

SUMMARY OF THE INVENTION

The present invention is an apparatus for producing an electrical stimulation signal adapted to be applied to a patient's jaw muscle thereby causing the jaw to open and preventing bruxism. Included are input means for receiving an input signal representative of jaw muscle activity. Control means are responsive to the input means and produce a control signal as a function of the input signal. Stimulator means responsive to the control means produce the electrical stimulation signal.

In preferred embodiments, the input signal is an electromyographic (EMG) signal indicative of electrical activity of the jaw muscle. The control means produces the control signal only when the EMG signal exceeds a threshold value indicative of a predetermined level of jaw muscle activity. Means for adjusting the threshold value are also included.

In other embodiments, the stimulator means includes a pulse generator for producing the stimulation signal in the form of a pulse train. Means for controlling intensity of pulses in the pulse train, as well as means for controlling the maximum intensity of the pulses, are included. Still other embodiments of the invention include means for recording the number of times the stimulator means produces the stimulation signal. A patients progress throughout a treatment program can thereby be monitored.

DETAILED DESCRIPTION OF THE PREFERRED EMBODIMENTS

Figure 1:
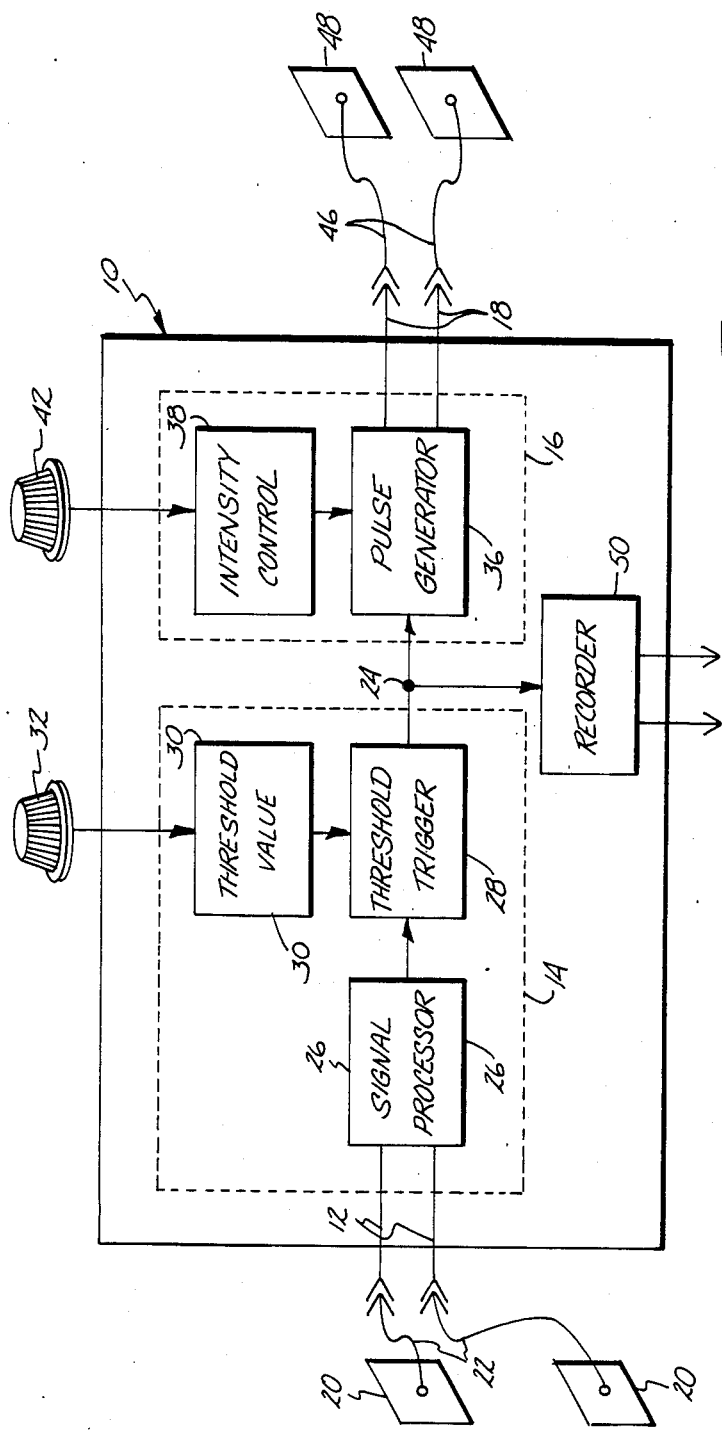
FIG. 1 is an electrical block diagram of the bruxism prevention apparatus of the present invention.

A preferred embodiment of the present invention is illustrated generally in FIG. 1. Bruxism prevention apparatus 10 is designed to produce an electrical stimulation signal which is adapted to be applied to a patient's jaw muscle. The stimulation signal causes the jaw to open and thereby prevents bruxism, as well as its harmful effects on the temporal mandibular joint and dental surfaces.

As shown in FIG. 1, apparatus 10 includes a plurality of input ports 12, control circuit 14, stimulator circuit 16, and a plurality of output ports 18. Input ports 12 (two are shown in FIG. 1) are adapted to receive an electrical input signal representative of to jaw muscle activity. In preferred embodiments, input ports 12 are adapted to receive an electromyographic (EMG) signal having a magnitude proportional to jaw muscle activity. The EMG signal can be sensed by electrodes 20 which are attached on or near the temporal mandibular joint of the jaw. Upon jaw tightening and/or clenching, electrodes 20 detect the EMG signal which is transmitted to input ports 12 through leads 22. While electrodes 20 are the preferred means for developing a signal representative of jaw muscle activity, other apparatus, including a pressure transducer positioned between the patient's teeth, or an externally mounted head halter with a transducer for detecting jaw movement, can also be used.

Control circuit 14 is configured to produce a control signal on control line 24 as a function of the input signal received on input ports 12. In the embodiment shown, control circuit 14 includes signal processing circuitry 26, threshold trigger circuit 28, and threshold value circuit 30. This embodiment of control circuit 14 produces the control signal as a step function of the input signal.

Signal processing circuitry 26 receives the input signal present on ports 12 and converts the signal into a usable form. Processing circuitry 26 can include amplifiers, filters, rectifiers or any other circuits commonly used for this function. In the embodiment shown, processing circuitry 26 produces a voltage signal having a magnitude proportional to the input signal.

Threshold trigger circuit 28 receives the processed input signal from signal processing circuitry 26 and compares the signal to a threshold value signal produced by threshold value circuit 30. When the processed input signal has a value equal or exceeding to that of the threshold value signal, threshold trigger circuit 28 generates the control signal on control line 24. The threshold signal produced by threshold value circuit 30 is preferably a voltage signal having a magnitude proportional to a predetermined level of jaw muscle activity. This signal is compared directly to the processed input signal by threshold trigger circuit 28.

The threshold value signal produced by threshold value control 30 can be adjusted by threshold control 32. Through control 32, the threshold value signal is adjusted to indicate a desired predetermined level of jaw muscle activity. Jaw muscle activity less than this level will not activate stimulator circuit 16. Control circuit 14 thereby functions as an EMG signal rejection circuit by producing the control signal on control line 24 only when a predetermined level of jaw muscle activity is sensed.

Stimulator circuit 16 produces the electrical stimulation signal as a function of the control signal received on control line 24. In the embodiment shown, stimulator circuit 16 includes pulse generator 36 and intensity control circuit 38. When triggered by the control signal, pulse generator 36 produces the stimulation signal in the form of a pulse train having a predetermined duration or period. Intensity of the pulses produced by pulse generator 36 is controlled by intensity control 38. A maximum intensity of the pulses produced by pulse generator 36 can be adjusted by maximum intensity control 42.

Figure 2:
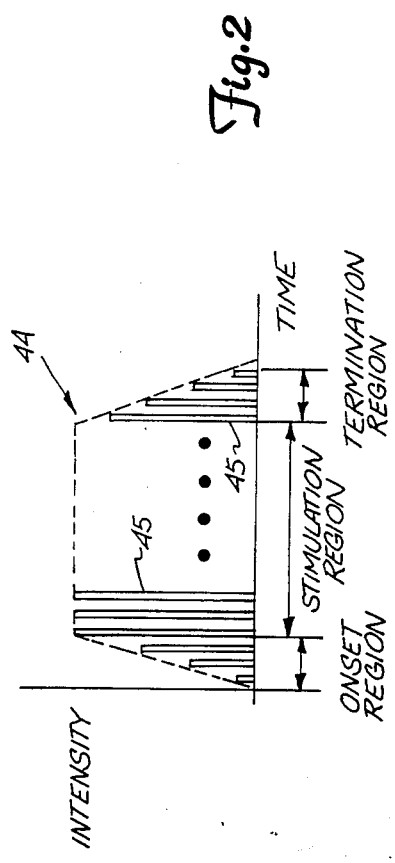
FIG. 2 is a time domain illustration of a stimulation signal produced by the bruxism prevention appratus shown in FIG. 1.
Figure 3:
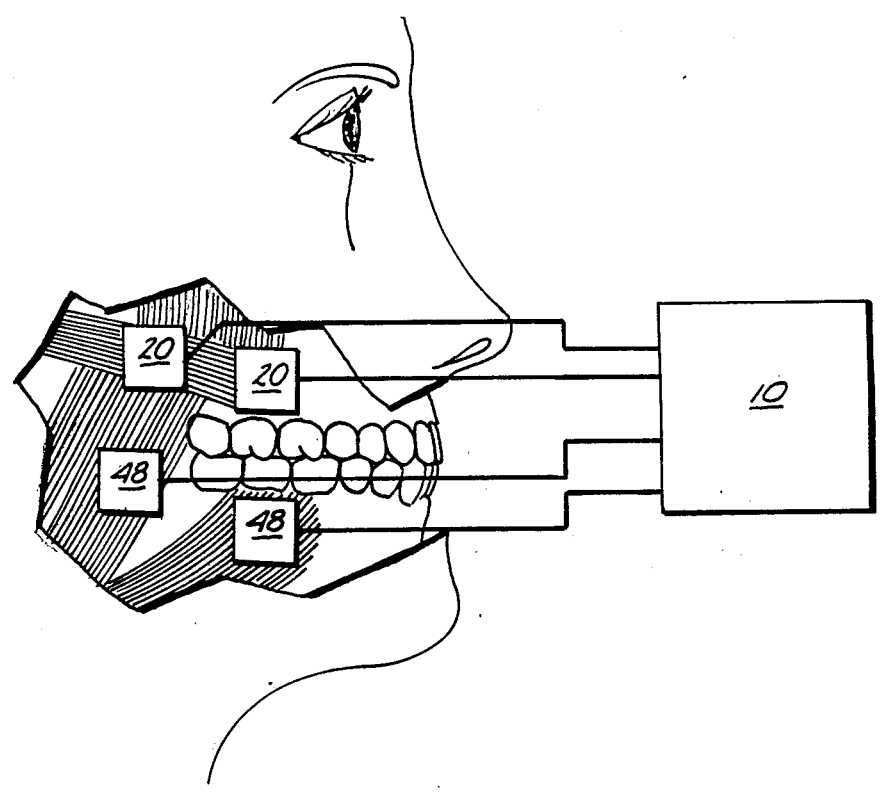
FIG. 3 is an an illustration of the bruxism prevention apparatus shown in FIG. 1 coupled to jaw muscles near the temporo-mandibular joint of a patient.

A preferred form of stimulation signal 44 produced by stimulator circuit 16 is shown in FIG. 2. Stimulation signal 44 is comprised of a series of voltage pulses 45 and includes an onset region, a stimulation region, and a termination region. During the onset region, intensity control 38 causes the voltage of pulses produced by pulse generator 36 to ramp upwards from a minimum voltage, 0 to 1 volt for example, to a maximum voltage set by maximum intensity control 42. Intensity control 38 causes the voltage of the pulses to remain at the maximum level throughout the stimulation region. During the termination region, intensity control 38 causes the voltage of the pulses to ramp downward until stimulator 16 is deactivated. Stimulator circuit 16 can then be retriggered by a control signal from control circuit 14.

In preferred embodiments, the onset region and termination region of stimulation signal 44 have a duration of one to three seconds. The stimulation region has a duration of five to ten seconds. Frequency of the pulses produced by pulse generator 36 can be from 5 to 35 pulses per second.

The stimulation signal present on output ports 18 is applied through leads 46 to electrodes 48 which are positioned on or near the patient's jaw muscle. When so applied, the stimulation signal will cause antagonistic muscle activity which forces the jaw to open. This action directly inhibits bruxism. In a preferred embodiment, the stimulation signal present on output ports 18 is applied to the jaw muscle through the same electrodes 20 used to detect the EMG signal.

As shown in FIG. 1, a preferred embodiment of bruxism prevention apparatus 10 includes recorder 50 which is connected to receive the control signal present on control line 24. Recorder 50 can also be interfaced with either control circuit 14 or stimulator circuit 16. Recorder 50 records information pertaining to the activity of apparatus 10. By way of example, recorder 50 can record the number of times during a given night that stimulator circuit 16 was triggered. Preferred embodiments of recorder 50 include magnetic or electronic memory. The recorded information can be used by a clinician to determine a patient's progress during a treatment program.

Although the present invention has been described with reference to preferred embodiments, workers skilled in the art will recognize that changes may be made in form and detail without departing from the spirit and scope of the invention. In particular, control circuit 14 can implement any desired functional relationship between the input signal received on ports 12, and the control signal produced on control line 24. Stimulation signal 44 can also take on other forms, including biphasic waveforms. All circuits described with reference to block diagrams are well known and easily implemented by those skilled in the art.

What is claimed is:

1. Apparatus for producing an electrical stimulation signal which can be applied to a patient's jaw muscle near the temporo-mandibular joint to cause the jaw to open and prevent bruxism, the apparatus comprising:
   input means for receiving an input signal representative of jaw muscle activity;
   control means responsive to the input means for producing a control signal as a function of the input signal; and
   stimulator means responsive to the control means for producing a jaw opening electrical stimulation signal.

2. The apparatus of claim 1 and including electrode means for sending an electromyographic (EMG) signal representative of jaw muscle activity, and for coupling the EMG signal to the input means.

3. The apparatus of claim 1 wherein the control means includes means for producing the control signal when the input signal exceeds a threshold value indicative of a predetermined level of jaw muscle activity.

4. The apparatus of claim 3 and further including means coupled to the control means for adjusting the threshold value.

5. The apparatus of claim 1 wherein the stimulator means includes pulse generator means for producing the stimulation signal in the form of a pulse train.

6. The apparatus of claim 5 and including means for controlling intensity of pulses in the pulse train.

7. The apparatus of claim 6 wherein:
   the pulse generator means comprises voltage pulse generator means for producing voltage pulses; and
   the means for controlling intensity of the pulses controls voltage of pulses in the pulse train.

8. The apparatus of claim 6 and including means for adjusting a maximum intensity of pulses in the pulse train.

9. The apparatus of claim 8 wherein the stimulator means includes means for producing a pulse train having a predetermined period.

10. The apparatus of claim 9 wherein:
    the stimulator means includes means for causing the predetermined period to include an onset region, a stimulation region, and a termination region; and
    the means for controlling the intensity of the pulses causes the intensity to increase to the maximum intensity during the onset region, to remain at the maximum intensity during the stimulation region, and to decrease during the termination region.

11. The apparatus of claim 1 and including electrode means for applying the electrical stimulation signal to the jaw muscle.

12. The apparatus of claim 1 and including means interfaced to the apparatus for recording information indicative of apparatus operation.

13. The apparatus of claim 12 wherein the means for recording information includes means for recording the number of times the stimulator means produces the stimulation signal.

14. Apparatus for preventing bruxism, comprising:
sensor means for sensing jaw muscle activity indicative of jaw clenching, and for providing a sensor signal representative thereof;
control means responsive to the sensor means for producing a control signal as a function of the sensor signal;
stimulator means responsive to the control means for producing a jaw opening electric stimulation signal; and
electrode means for applying the stimulation signal to the jaw muscle near the temporo-mandibular joint.

15. The apparatus of claim 14 wherein the sensor means comprises electrodes for sensing an electromyographic (EMG) signal within the jaw muscle.

16. The apparatus of claim 15 wherein:
the control means includes means for producing the control signal only when the sensor signal has at least a predetermined magnitude; and
the stimulator means includes means for producing the stimulation signal only in response to the control signal.

17. The apparatus of claim 16 and including means coupled to the control means for adjusting the predetermined magnitude of the sensor signal which must be provided before the control means produces the control signal.

18. The apparatus of claim 14 wherein the stimulator means includes pulse generator means for producing the stimulation signal in the form of a pulse train.

19. The apparatus of claim 18 wherein a frequency of pulses in the pulse train is from five to thirty-five pulses per second.

20. The apparatus of claim 18 and including means for controlling intensity of pulses in the pulse train.

21. The apparatus of claim 20 and including means for adjusting a maximum intensity of pulses in the pulse train.

22. The apparatus of claim 21 wherein the means for controlling intensity controls voltage of pulses in the pulse train.

23. The apparatus of claim 22 wherein:
the stimulator means includes means for causing the pulse train to have a predetermined period which includes an onset region, a stimulation region, and a termination region; and
the means for controlling intensity includes means for causing voltage of the pulses to increase to the maximum voltage during the onset region, to remain at the maximum voltage during the stimulation region, and to decrease from the maximum voltage during the termination region.

24. The apparatus of claim 23 wherein:
the stimulator means causes the onset region and termination regions to have a duration of one to three seconds; and
the stimulator means causes the stimulation region to have a duration of five to ten seconds.

25. The apparatus of claim 14 and including means interfaced to the apparatus for recording information regarding apparatus operation.

26. The apparatus of claim 25 wherein the means for recording information includes means for recording the number of times the stimulator means produces the stimulation signal.

27. A method for preventing bruxism including:
sensing jaw muscle activity indicative of jaw clenching; and
applying a jaw opening electrical stimulation signal to jaw muscles when clenching is sensed.

28. The method of claim 27 and sensing electromyographic (EMG) signals within the jaw muscle to indicate jaw clenching.

* * * * *